United States Patent [19]
Lehmikangas et al.

[11] Patent Number: 4,895,019
[45] Date of Patent: Jan. 23, 1990

[54] PROCEDURE FOR MEASURING THE RELATIVE QUANTITIES OF PULP COMPONENTS IN WOOD OR PAPER PULP

[75] Inventors: Keijo Lehmikangas; Jouni Tornberg, both of Kajaani, Finland

[73] Assignee: Kajaani Elecktroniikka OY, Kajaani, Finland

[21] Appl. No.: 189,430

[22] Filed: May 2, 1988

[51] Int. Cl.$^4$ .......................................... G01N 33/46
[52] U.S. Cl. ........................................................ 73/63
[58] Field of Search ................................. 73/63, 61 R

[56] References Cited

U.S. PATENT DOCUMENTS

| | | | |
|---|---|---|---|
| 3,873,416 | 3/1975 | Forgacs et al. | 73/63 X |
| 4,276,119 | 6/1981 | Karnis et al. | 73/61 R X |
| 4,342,618 | 8/1982 | Karnis et al. | 73/61 R X |

FOREIGN PATENT DOCUMENTS 275499 10/1970 U.S.S.R. ................................... 73/63

Primary Examiner—Michael J. Tokar
Assistant Examiner—Joseph W. Roskos
Attorney, Agent, or Firm—Bierman and Muserlian

[57] ABSTRACT

A procedure for measuring the relative quantities of pulp components in wood or paper pulp, wherein
for the pulp components (a,b) present in the pulp, for each one separately, is measured the distribution, or probability density, function ($b_a$, $b_b$) of a given fibre-specific characteristic thereof,
from the distribution functions are by calculation formed distribution functions ($b_{a/b}$) corresponding to the pulp mixture,
the distribution function ($b_{x/y}$) of the corresponding characteristic of the pulp is measured, and
by calculation are determined the correlations of the distribution function ($b_{x/y}$) of the pulp under examination with the distribution functions ($b_{a/b}$) found by calculation, for determining the proportions of the different pulp components.

7 Claims, 2 Drawing Sheets

PROCEDURE FOR MEASURING THE RELATIVE QUANTITIES OF PULP COMPONENTS IN WOOD OR PAPER PULP

The present invention concerns a procedure for measuring the relative quantities of different components (e.g. softwood/hardwood, cellulose/groundwood) in wood or paper pulp.

Wood or paper pulp consists of a plurality of pulp components, depending on the quality requirements imposed on the end product. The differences in characteristics between the different components are due not only to differences in raw material (e.g. hardwood/softwood) but also on the defibration method. In chemical defibration (digestion, or cooking) the fibres are detached from each other intact, and the adaptability of the fibre increases. In mechanical defibration (grinding, hot grinding) in contrast, fibres are broken and fines are produced at the same time.

It is important in view of optimizing the properties of the end product, to know the relative contributions of different components to the mixture. Also associated herewith is the determination of the fibre proportions in each individual pulp component—for instance: how high is the content of short hardwood cellulose (which presents poorer strength characteristics) among the long-fibre softwood cellulose. Cellulose makers furthermore control the species exchange (pine→birch) by determining the hardwood percentage. If one is able to determine the softwood/hardwood fibre proportion accurately and rapidly, considerable savings are achieved because the share of mixed pulp becomes less and the amount of softwood fibre present among hardwood pulp can be minimized.

The traditional procedure serving determination of pulp components is to make a count, with the aid of a microscope, of the different kinds of fibres in a stained fibre preparation. This procedure is cumbersome and time-consuming and requires a person versed in its use.

The procedure of the present invention is based on using, in determining the pulp components, a characteristic measured fibre-specifically from the wood pulp, and certain density functions established by measurements. The quantity measured from the wood pulp is, most advantageously, the fibre length; it may however equally be the fibre-individually measured fibre thickness, wall thickness, lightness of colour, lignin content, or another property characteristic of each kind of pulp which is measurable from the different pulps with adequate accuracy. The relative quantities of the components are calculated, applying correlation techniques.

In the procedure of the invention the distributions, or probability functions, of a given, selected characteristic of those pulp components of which the proportion in a given mixture has to be determined, are measured from equivalent, pure specimens, and the corresponding distribution functions are formed by calculation for the pulp mixture. A measurement is furthermore made of the distribution function of the respective characteristic in the pulp under examination, whereafter the proportions of different kinds of pulp in the pulp under examination containing said pulp components are determined by calculating the correlations of the distribution function of the pulp under examination with those established by calculation.

Figure 1:
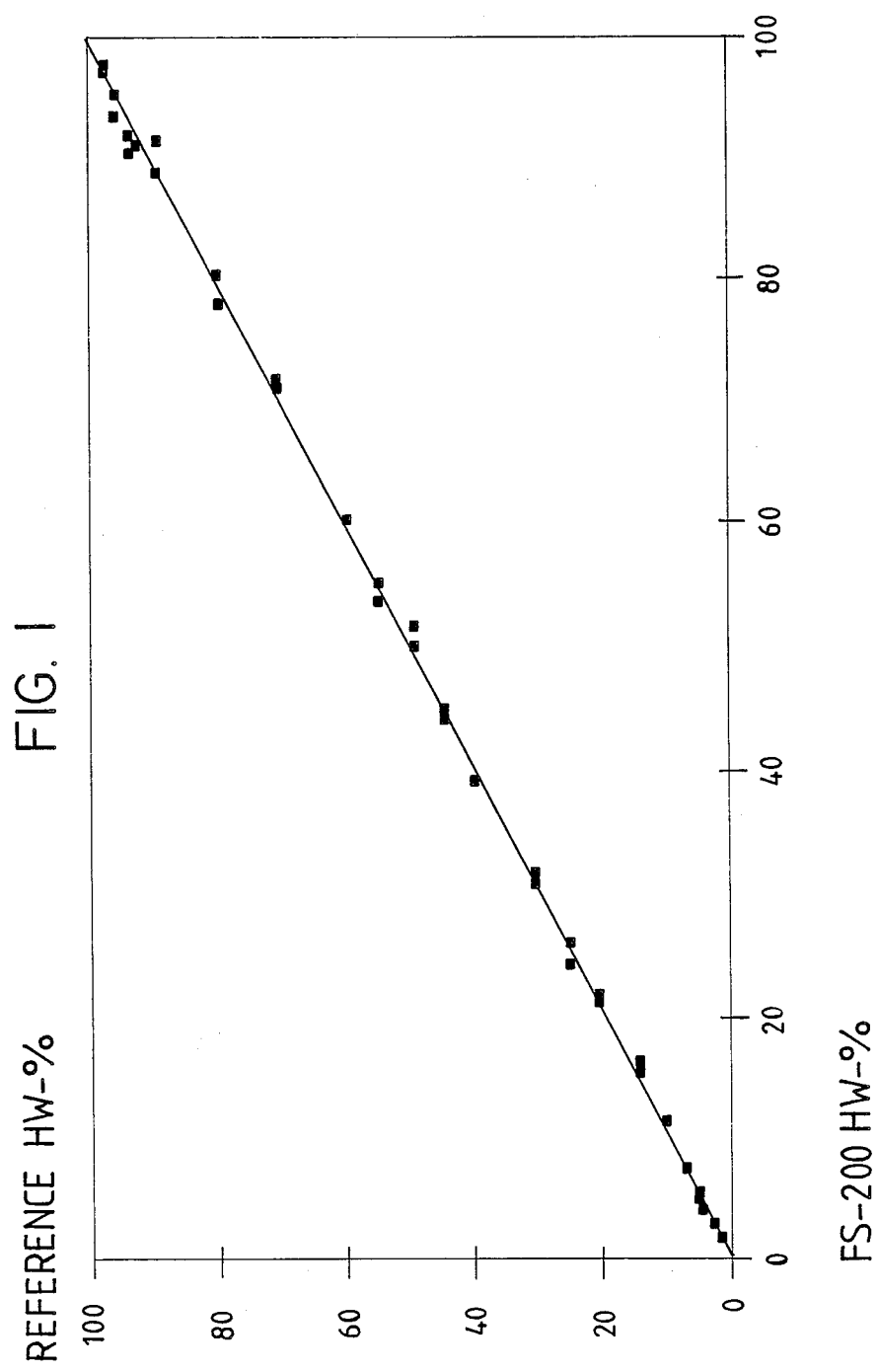
FIG. 1 is a graph plotting the measuring results obtained when measuring the relative quantity of birch pulp (HW) and pine pulp (FW$_2$) with the method of the claimed invention.
Figure 2:
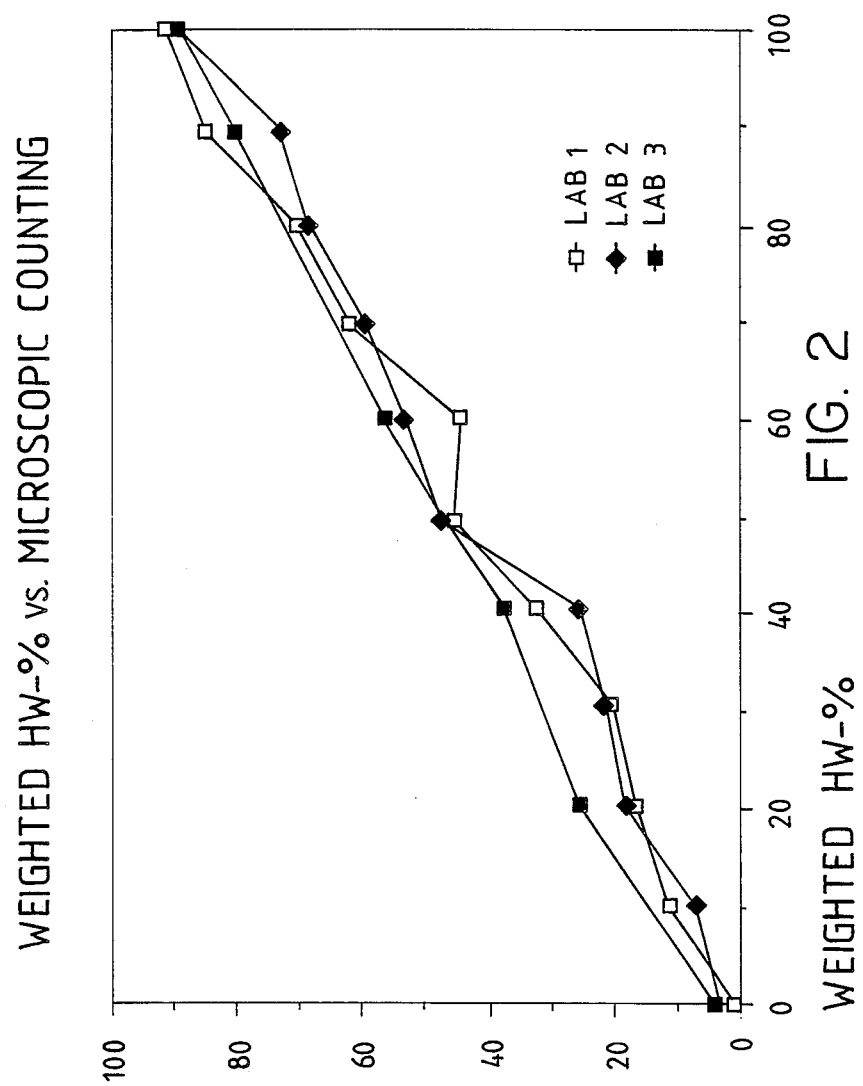
FIG. 2 is a graph of the measured results obtained when using the microscope procedure of the same method with the birch pulp and pine pulp.

In calculating the correlations, one may use Rank's correlation formula:

$$r_{rank} = 1 - 6 \cdot \sum_{l}^{N} D_i^2 / N(N^2 - 1) \tag{1}$$

where $r_{rank}$ = Rank's coefficient of correlation
$D_i$ = Difference between the distribution curves in the length class $N_i$ ($I = 1 \ldots N$).
$N$ = Total number of length classes.

Maximum correlation is obtained with that value of the proportions of pure specimens which comes closest to the proportion that is being determined.

In an embodiment of the invention, the distributions corresponding to different pulp mixtures are formed from the distribution functions of a given characteristic with a selected set of pulp proportions, e.g. in 5% steps (5/95, 10/90, 15/85, ..., 95/5). It is thereafter possible to determine the proportions of different kinds of pulp in the unknown sample under measurement which contains the above pulp components, by calculating the correlations between the distribution function of the pulp under examination and the above distribution functions established by calculation in 5% steps.

In a situation encountered in actual practice the above resolution of 5% does not give adequate accuracy of measurement: an accuracy about 1% is required. Of course, the measurement could be carried out by calculating $P_{a/b}$ functions in steps of 1% and performing a calculation of correlation with each one of the 100 functions. This is however a slow operation, owing to the great number (100) of correlations which must be calculated. Significantly higher speed of calculation can be achieved on the basis of the knowledge that the calculated correlation function $r(p_{x/y})$ is parabolic. The correlation may then be calculated for only three values of a/b, e.g. the values 10/90, 50/50 and 90/10, and the equation of the parabola passing through these points $r(p_{x1/y1})$, $r(p_{x2/y2})$, $r(p_{x3/y3})$ can be formed:

$$r(p_{x/y}) = k \cdot x^2 + l \cdot x + m \tag{2}$$

where k, l, m are the coefficients of the parabola.

The coefficients are found by solving the following simultaneous equations:

$$r(p_{x1/y1}) = k(x1)^2 + l \cdot x1 + m \tag{3}$$

$$r(p_{x2/y2}) = k(x2)^2 + l \cdot x2 + m \tag{4}$$

$$r(p_{x3/y3}) = k(x3)^2 + l \cdot x3 + m \tag{5}$$

The maximum of the correlation function is now readily found by determining the zero of the first derivate of the parabola, i.e., $$r'(p_{x/y}) = 2kx + l = 0 \tag{6}$$

Thus, $$x = -\tfrac{1}{2}k = -\tfrac{1}{2} \cdot (l/k) \tag{7}$$

l and k can be solved from equations (3) to (5). y can be found in like manner, or since we know that the sum of components constitutes the total mass, we find: y(%)=100−x(%).

The procedure of the invention can also be expanded to be applied in measurement of more than two components. The calculations proceed in that case in the manner that calculation of two of the components is performed with the method just described by comparing the unknown sample with a calculated mixture of two pure specimens and the ratio of these two unknown is thus obtained. By varying, in the calculation, these pure pulps under examination a sufficient number of mutual proportions is found from which the overall proportions can be derived.

Taking for example the proportion x/y/z of three pulp components:

Measurement made of $x/y = A/B$ and $y/z = C/D$

Hence $x/y/z = A/B/(B \cdot D/C)$

The measurement may also be accomplished in that e.g. in the case of three components the unknown sample under measurement is compared with a group of distributions formed by calculation from three pure specimens, one of the specimens serving as a parameter and the other two being varied. Three changes of the parameter enable correlation graphs to be established with each parameter, and their intersection will now indicate the quantitative proportions of the different kinds of pulp.

In the foregoing the invention has been described by referring to certain embodiments thereof. However, the procedure of the invention is not exclusively confined to these embodiments: it may vary within the scope of the inventive idea delimited by the claims following below.

We claim:

1. A method for measuring the relative amounts of different pulp components in a pulp mixture comprising determining for the individual pulp components the distribution function of a given fiber specific characteristics for each pulp, calculating from the distribution functions obtained the distribution functions corresponding to the pulp mixture, measuring the distribution function of the corresponding characteristic of the pulp mixture and determining the proportions of the different pulp components by correlation of the distribution function of the pulp under examination with the distribution functions obtained by the calculation.

2. Method accoridng to claim 1, characterized in that the distribution functions ($b_{a/b}$) corresponding to the pulp mixture are formed in certain increments.

3. The method of claim 2 wherein the increments are increments of 5%.

4. Method according to claim 1 characterized in that the correlations are calculated for three values of the pulp components a,b present in the pulp from which is formed the correlation function (a parabola) on the basis of its maximum being found the proportion of the pulp components.

5. Method according to claim 1, characterized in that in measurement of more than two components: calculation is first performed concerning two components, by comparing the pulp under examination with a mixture of two pure components, whereby the ratio of these two unknown is found; the pair of pulps under consideration is changed and corresponding measurements are preformed; and after (n−1) measurements (n=number of pulp components) the overall proportions are calculated from the binary ratios that have been obtained.

6. Method according to claim 1, characterized in that the characteristic that is measured is the fibre length.

7. Method according to claim 1, characterized in that the characteristic that is measured is the fibre thickness, wall thickness, lightness of colour or lignin content.

* * * * *